United States Patent [19]
Giles, Jr.

[11] Patent Number: 5,977,120
[45] Date of Patent: Nov. 2, 1999

[54] COMPOSITION FOR ACHIEVING AN ALERT, YET CALM STATE

[76] Inventor: James A. Giles, Jr., 2030 - 29th St., San Diego, Calif. 92104

[21] Appl. No.: 09/193,939

[22] Filed: Nov. 17, 1998

[51] Int. Cl.⁶ .......................... A61K 31/52; A61K 31/35; A61K 35/78
[52] U.S. Cl. .......................... 514/264; 514/262; 514/263; 514/460; 424/195.1
[58] Field of Search ..................... 514/262, 263, 514/264, 460; 424/195.1

[56] References Cited

U.S. PATENT DOCUMENTS

| | | | |
|---|---|---|---|
| 5,273,754 | 12/1993 | Mann | 424/440 |
| 5,296,224 | 3/1994 | Schwabe | 424/195.1 |
| 5,770,207 | 6/1998 | Bewicke | 424/195.1 |

*Primary Examiner*—Raymond Henley, III
*Attorney, Agent, or Firm*—Baker & Maxham; Peter R. Martinez

[57] ABSTRACT

Compositions and a method for promoting an alert state without promoting anxiety, comprising at least one kavalactone and at least one methylxanthine. The compositions balance the energizing effects of methylxanthine stimulants with the calming effects of kavalactone relaxants. The compositions of the invention are presented in a variety of formulations, with or without other active ingredients such as vitamins and minerals.

21 Claims, No Drawings

COMPOSITION FOR ACHIEVING AN ALERT, YET CALM STATE

BACKGROUND OF THE INVENTION

1. Field of the Invention

The present invention relates generally to dietary supplements, and more particularly, to a composition comprising kava and caffeine that produces an alert, yet calm state in a host subject.

2. Discussion of the Related Art

Throughout history, humans have consumed a wide variety of substances to affect their mental or physical state. Our modern non-stop society places ever increasing demands on our time, and many people consume stimulants to keep them wakeful and attentive for extended periods. These stimulants can cause overstimulation, so many people use relaxants of various types. Unfortunately, the relaxants and stimulants do not act synergistically, and the individual swings from an over-stimulated condition to an over-sedated condition.

The most widespread stimulant is caffeine, which is primarily ingested by drinking tea or coffee. Caffeine affects the central nervous system, mainly the cerebrum. Caffeine is found in coffee beans, tea, cola nuts, guarana, cacao seeds, and mate. Caffeine can also be manufactured synthetically. The chemical name for caffeine is 1,3,7-trimethylxanthine. Other common methylxanthine stimulants include 1,3-dimethylxanthine (found in tea and commonly called theophylline), and 3,7-dimethylxanthine (found in cacao seeds and tea, and commonly called theobromine).

Products containing caffeine are ubiquitous. A sampling of such products includes coffees, teas, soft drinks, chocolate products, cold-relief products, diet aids, various foods including puddings and, of course, products specifically designed to keep people awake and alert.

Although caffeine is employed in countless products, it can have undesirable side effects. The most common side effect is a general "jittery" feeling, but other side effects include restlessness, nervousness, gastro intestinal disturbances, muscle twitching, and in some extreme cases, cardiac arrhythmia.

A relaxant that is in widespread use today is kava. Kava, also known as kava-kava, yaquona, ava, ava-ava, awa, or kawa, is a member of the pepper family Piperceae. Kava is obtained from the rhizome and roots of *Piper methysticum Forst*. Kava is the most relaxing botanical herb with the exception of the opium poppy. Kava is known to induce general relaxation in humans when orally ingested, but it does not cause drowsiness or involuntary sleep. A liquid macerate of the kava root has been used on islands in the South Pacific in social gatherings and religious rituals for over three thousand years.

Recently, kava has been scientifically scrutinized and its psychoactive ingredients identified. These ingredients are referred to as kavalactones. A total of fifteen kavalactones have been identified to date, including kavain (a.k.a. kawain), dihydrokavain (a.k.a. dihydrokawain), methysticin, dihydromethysticin, yangonin, and demethoxy-yangonin. A synthetic version of kava, known as D,L-kavain is also available.

The specific kavalactones in kava root extract vary depending upon the origin of the kava plant. Further, the particular kavalactones present depend upon what part of the plant is used to prepare the extract. Kava roots, and their rhizomes, or distal root tips, are preferred, but other parts of the plant can be used. High quality extracts of kava are sold based upon the total kavalactone content, rather than upon analysis of the individual lactones contained therein.

Studies indicate that kavalactones can relieve nervous anxiety, tension, restlessness, as well as promote muscle relaxation. Studies have also shown that consumption of kavalactones does not impair neurophysiological activity, as evidenced by measurements of recognition rates, and driving ability. Further, kavalactones are non-addictive and do not induce involuntary sleep or symptoms of drunkenness. The German Commission E, a government-appointed panel that reviews herbal remedies, has approved kava to relieve anxiety and stress without side effects.

Traditionally, kava root is prepared for human consumption by pulverizing the root and/or rhizome and mixing it with water to obtain a liquid which can be consumed orally. Presently, kava root extracts are manufactured using ethanol as a solvent, as the kavalactones are readily soluble in ethanol. The extracted material is a yellowish brown paste or powder, which is tested to determine the weight percentage of kavalactones. Synthetic versions of kava are also available.

Today, kava is widely available as an herbal supplement in the form of pills, tablets and capsules made of pharmaceutical grade extract. For example, kava root extract is commercially available in single dose formulations containing from about 2% by weight to 30% by weight (i.e., 2% to 30% by wt) active kavalactones.

In view of the foregoing, it would be highly desirable to provide a dietary supplement having a stimulatory effect coupled with a general calming effect, thereby producing a synergistic combination that allows individuals to remain awake and efficient, but also composed and relaxed.

SUMMARY OF THE INVENTION

In accordance with the present invention, compositions are provided that comprise kavalactones and methylxanthines. The compositions of the present invention balance the energizing effects of methylxanthines with the calming effects of kavalactones. The compositions of the invention are used for promoting an alert state in a host subject without promoting anxiety. The invention compositions can additionally contain other ingredients such as vitamins and minerals and may be provided in a variety of formulations.

DETAILED DESCRIPTION OF THE PREFERRED EMBODIMENTS

The compositions of the invention comprise kavalactones and methylxanthines in synergistic combinations that produce a wakeful, yet tranquil state. The stimulant employed in the compositions is a methylxanthine, or mixtures of methylxanthines. A preferred stimulant is caffeine (1,3,7-trimethylxanthine) which can be obtained from coffee beans, tea leaves, cola nuts, guarana, cacao seeds, or mate. Synthetic caffeine may also be utilized in the present invention. Additional methylxanthines that may be used in the present invention include 1,3-dimethylxanthine (present in tea) and 3,7-dimethlxantine (present in cacao), as well as mixtures thereof.

Caffeine (1,3,7-trimethylxanthine) is available from well known sources such as coffee beans, tea leaves, cola nuts and cacao seeds. For example, the caffeine in chocolate, cocoa, and cocoa butter is obtained from cacao seeds. Less well known sources of caffeine are guarana and maté. Maté is made from a South American evergreen tree (*Ilex*

*paraguariensis*) whose leaves contain caffeine. Mate is customarily consumed as a tea-like beverage. Guarana is a vine that climbs trees in South America, and grows as a shrub when cultivated in the open. The botanical name is *Paullinia cupana* H.B.K., variety *sorbilis*. Seeds cultivated from the plant yield guaranine, which has the same chemical composition as caffeine. A syrup extract is obtained from the seeds and used in soft drinks, or the seeds can be roasted and ground into powder.

The anti-anxiety, or relaxing components of the compositions of the invention are kavalactones, and include kavain (a.k.a. kawain), dihydrokavain (a.k.a. dihydrokawain), methysticin, dihydromethysticin, yangonin, and demethoxyyangonin, among others. Kavalactones are obtained from the dried rhizome and roots of the kava plant. A pharmaceutical grade kava root extract, standardized to provide a kavalactone content of about 30% by wt and containing the full spectrum of lactones found in the kava plant may be employed in the compositions of the invention. However, lower or higher kavalactone contents (from 2% to 50% by wt) may also be used. A synthetic version of kava may also be utilized. This synthetic version comprises both the D and L forms. The individual kavalactones may be obtained commercially and utilized individually or combined to provide all of the kavalactones present in the native plant.

Compositions of the present invention may be formulated for administration to any suitable subject (human or animal) by any conventional route such as oral, rectal, or nasal. Thus the composition may be a tablet, capsule, suspension, emulsion, solution, suppository, or spray. The composition can be formulated to provide a homogenous mixture, or the composition can be formulated so that the kavalactone component and the methylxanthine component are non-homogenous.

Formulations for oral use include tablets or capsules which contain the active ingredients mixed optionally with pharmaceutically acceptable inert excipients. Such excipients include for example: inert diluents such as calcium carbonate, sodium chloride, lactose, calcium phosphate, sodium phosphate, etc.; granulating and disintegrating agents, for example, potato starch, alginic acid, etc.; binding agents, for example, starch, gelatin or acacia, etc.; and lubricating agents for example, magnesium stearate, stearic acid or talc. Other pharmaceutically acceptable excipients include colorants, flavoring agents, plasticizers, humectants, etc. Tablets provided in accordance with the present invention may be uncoated or they may be coated by known techniques.

Alternatively, the active ingredients of the present invention may be delivered over an extended time period by delaying disintegration and absorption in the gastrointestinal tract to provide a sustained release effect. A time delay material such as glyceral monostearate or glycerol distearate may be employed for this purpose. Extended release formulations that may be employed to deliver the active ingredients of the invention are well known in the art. See, for example, Baker, Richard, Controlled Release Of Biologically Active Agents, John Wiley And Sons, 1986.

In certain embodiments, the active ingredient(s) may be delivered in a soft or hard gel capsule by mixing the active ingredient with water or an oil such as peanut oil, or olive oil and enclosing the resulting formulation in a capsule.

The dosage may also be administered as an oral liquid dosage form by suspending the active ingredients or extracts thereof in an aqueous solution in admixture with a dispersing or wetting agent, suspending agent and one or more preservatives. Suitable dispersing or wetting agents are, for example, naturally occurring phosphatides, for example, lecithin, or condensation products of ethylene oxide, fatty acids, long chain aliphatic acids, or a partial ester derived from fatty acids and a hexitol or hexitol anhydrides, for example, polyoxyethylene stearate, polyoxyethylene sorbitol monooleate, polyoxyethylene sorbitan monooleate, etc. Suitable suspending agents are, for example, sodium carboxymethylcellulose, methylcellulose, sodium alginate, etc.

For rectal applications, suitable formulations for compositions according to the present invention include suppositories (emulsion or suspension type), and rectal gelatin capsules (solution or suspensions). In a typical suppository formulation, the active ingredients are combined with an appropriate pharmaceutically acceptable suppository base such as cocoa butter, esterified acids, glycerinated gelatin, and various water soluble or dispersable bases like polyethylene glycols and polyoxyethylene glycols and polyoxyethylene sorbitan fatty acid esters.

One embodiment of the invention comprises a composition containing about 50 to 350 mg kava root extract—containing about 2% to 50% by weight kavalactones—and about 50 to 250 mg caffeine—containing about 10% to 100% by weight 1,3,7-trimethylxanthine. In another embodiment, 1,3-dimethylxanthine or 3,7-dimethylxanthine can be substituted for 1,3,7-trimethylxanthine.

An alternative embodiment of the present dietary supplement comprises kava root extract and caffeine in about a one-to-one ratio of active ingredients. Other embodiments may vary the ratio of active ingredients from: one part kava to nine parts caffeine, to: nine parts kava to one part caffeine.

A preferred formulation would comprise about 100 mg kava root extract (containing about 30% by wt kavalactones), and 100 mg caffeine (containing anywhere from about 30% by wt to 100% by wt 1,3,7-trimethylxanthine) in a capsule or tablet with any necessary inert excipients. Another preferred embodiment would contain 200 mg kava root extract (with about 30% by wt kavalactones), and 200 mg caffeine (containing anywhere from about 30% by wt to 100% by wt 1,3,7-trimethylxanthine) in a capsule or tablet, with any necessary inert excipients.

Alternatively, the formulation may contain only one component, either kava, or caffeine in the above-described ranges, with both components packaged together, thus allowing more flexibility in individual dosages. For example, the present dietary supplement may comprise capsules or tablets containing 50 mg kava root extract (with about 30% by wt kavalactones) and capsules or tablets containing 50 mg caffeine (containing anywhere from about 30% by wt to 100% by wt 1,3,7-trimethylxanthine), packaged together so that the ratio of the two components can be varied to achieve the desired effect of an alert, yet calm state. Other embodiments Throughout the above description, the preferred embodiment and other examples should be considered as exemplars, rather than as limitations on the present invention. While I have described the invention by means of specific embodiments, it is to be understood that numerous changes and modifications may be made therein without departing from the spirit and the scope of the invention as shown in the appended claims. Accordingly, it is appropriate that the appended claims be construed broadly and in a manner consistent with the spirit and scope of the invention herein described.

What is claimed is:

1. A composition for promoting an alert state without promoting anxiety, comprising:
    at least one kavalactone; and
    at least one methylxanthine.

2. A composition according to claim 1, wherein said kavalactone is obtained from *Piper methysticum*.

3. A composition according to claim 1, wherein the kavalactone is selected from the group consisting of kavain, kawain, dihydrokavain, dihydrokawain, methysticin, dihydromethysticin, yangonin, demethoxyyangonin and mixtures thereof.

4. A composition according to claim 1, wherein said kavalactone is obtained synthetically.

5. A composition according to claim 1, wherein said methylxanthine is selected from the group consisting of 1,3,7-trimethylxanthine, 1,3-dimethylxanthine, 3,7-dimethylxanthine and mixtures thereof.

6. A composition according to claim 1, wherein said methylxanthine is obtained synthetically.

7. The composition of claim 1, further comprising at least one substance selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and bulking agents.

8. A composition comprising kava and caffeine in a ratio effective for inducing an alert, yet calm state.

9. A composition according to claim 8, wherein the ratio of kava to caffeine ranges from 1:10 to 10:1.

10. A composition according to claim 8, wherein the caffeine is obtained from at least one natural substance selected from the group consisting of coffee beans, tea leaves, cola nuts, guarana, cacao seeds and mate.

11. A composition according to claim 8, wherein the caffeine is synthetically produced.

12. The composition of claim 8, wherein the caffeine contains from about 10% to 100% by weight 1,3,7-trimethylxanthine.

13. A composition according to claim 8, wherein said kava is obtained from the *Piper methysticum* and comprises at least one kavalactone selected from the group consisting of kavain, kawain, dihydrokavain, dihydrokawain, methysticin, dihydromethysticin, yangonin, and demethoxyyangonin or mixtures thereof.

14. The composition of claim 8, wherein said kava is present as a root extract containing from about 2% to 50% by weight active kavalactones.

15. The composition of claim 8 in a sustained release form.

16. The composition of claim 8, and further comprising at least one substance selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and bulking agents.

17. The composition of claim 8, wherein the kava and the caffeine is a non-homogenous mixture.

18. A synergistic composition for promoting an alert yet calm state, comprising:
    about 2% to 40% by weight kavalactones selected from the group consisting of kavain, kawain, dihydrokavain, dihydrokawain, methysticin, dihydromethysticin, yangonin, demethoxyyangonin and mixtures thereof, and
    about 50% to 100% by weight methylxanthine selected from the group consisting of 1,3,7-trimethylxanthine, 1,3-dimethylxanthine and 3,7-dimethylxanthine.

19. The composition of claim 18, further comprising at least one substance selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and bulking agents.

20. A method for promoting an alert state without promoting anxiety in a host subject, comprising:
    administering a composition comprising at least one kavalactone and at least one methylxanthine.

21. The method of claim 20, and further comprising the step of adding at least one substance to the composition selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and bulking agents.

* * * * *